United States Patent [19]

Itoh et al.

[11] Patent Number: 4,656,162
[45] Date of Patent: Apr. 7, 1987

[54] METHOD FOR CONTROLLING SANITARY AND AGRICULTURAL PESTS

[75] Inventors: Koichi Itoh; Yoshiaki Nishimura, both of Tokyo, Japan

[73] Assignee: Shin-Etsu Chemical Co., Ltd.

[21] Appl. No.: 670,743

[22] Filed: Nov. 13, 1984

[51] Int. Cl.⁴ .............................................. A01N 55/00
[52] U.S. Cl. ..................................................... 514/63
[58] Field of Search ........................... 424/184; 514/63

[56] References Cited

U.S. PATENT DOCUMENTS 4,146,619  3/1979  Lover et al. .......................... 424/184
4,352,833  10/1982 Young et al. ......................... 424/184

FOREIGN PATENT DOCUMENTS 916561  1/1963  United Kingdom ................. 424/184
926914  5/1963  United Kingdom ................. 424/184

OTHER PUBLICATIONS

Derwent 256, Japan 84-148574/24, published 3-5-84.
Chemical Abstracts 92:192752r (10 Jan. 80).
Chemical Abstracts 90:67756c (14 Dec. 78).
Chemical Abstracts 66:75273n (20 Nov. 66).

Primary Examiner—Albert T. Meyers
Assistant Examiner—John M. Kilcoyne
Attorney, Agent, or Firm—Toren, McGeady and Goldberg

[57] ABSTRACT

The invention provides a novel method for controlling various kinds of pests harmful against sanitation and agriculture by applying an organosilicon compound, never used hitherto for such a purpose, to the body of the pest or distributing the compound over the site or field infested therewith. The organosilicon compound which is an organosilane or organopolysiloxane compound, is characterized by at least one (poly)oxyalkylene group bonded to the silicon atom in a molecule and advantageously has no toxicity against human body.

2 Claims, No Drawings

METHOD FOR CONTROLLING SANITARY AND AGRICULTURAL PESTS

BACKGROUND OF THE INVENTION

The present invention relates to a novel method for controlling sanitary and agricultural pests or, more particularly, to a method for controlling sanitary and agricultural pests using a relatively inexpensive compound having absolutely no toxic effect to mammals including man and useful or domestic animals and not used hitherto as an insecticide.

Needless to say, a great number of synthetic and naturally occurring compounds have been proposed and practically used as an insecticide to control the population of various pests, i.e. noxious insects, harmful against sanitation of human life and agricultural art including forestry, horticulture and the like. Most of the prior art insecticidal compounds are expensive which limits the applicability of the compound from the economic standpoint. Moreover, in recent years, certain species of insects exposed to a particular insecticide compound rapidly acquire strong resistance against the compound so that the insecticidal effect initially expected to the compound is lost within a relatively short period of time after the insecticide compound has come into practical application.

Even worse, most of the hitherto known insecticide compounds or especially those prepared synthetically are not free from the problem of toxicity to the human body and domestic animals and accumulation of insecticide compounds in the environment is one of the problems of very serious public concern from the standpoint of environmental protection.

Thus, it is eagerly desired to develop a method for controlling ectoparasitic or non-ectoparasitic pests on human and animal bodies or household sites as well as agricultural pests in the field without the problems of high cost acquired resistance and toxicity of the insecticide compound.

Recently, a pediculicidal method has been disclosed in U.S. Pat. No. 4,146,619 according to which a linear organosiloxane polymer having repeating units $R_2SiO$ in which each R is an alkyl or aryl group and having a viscosity of less than about 20,000 centistokes is applied to an animal or human. This method is, however, not effective for controlling ectoparasites and their ova and, moreover, less effective for controlling pests other than lice.

SUMMARY OF THE INVENTION

It is therefore an object of the present invention to provide a novel method for controlling pests which are harmful to humans and animals and agricultural pests in the fields while avoiding the problems of cost, acquired resistance and toxicity of the insecticide compound to mammals.

Thus, the method of the present invention for controlling pests harmful to humans and agriculture comprises applying an organosilicon compound having, in a molecule, at least one (poly)oxyalkylene group represented by the general formula

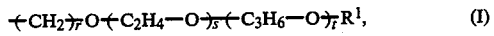  (I)

in which $R^1$ is a hydrogen atom or a monovalent hydrocarbyl or acyl group and the suffixes r, s and t are each zero or a positive integer with the proviso that s and t are not simultaneously equal to zero, bonded to the silicon atom therein, to the body of the pest or distributing the organosilicon compound over the site or field infested with the pests.

More particularly, the organosilicon compound mentioned above is an organosilane or organopolysiloxane compound represented by the general formula

  (II)

in which the suffixes m and n are each zero or a positive integer, R is a hydrogen atom, a hydroxy group or a monovalent hydrocarbyl group, at least one of the groups R in a molecule being a monovalent hydrocarbyl group, G is a (poly)oxyalkylene group represented by the general formula (I) given above and $G^a$ is the same group as R or G, at least one of the groups denoted by $G^a$ being G when n is equal to zero. This organosilicon compound should preferably have a viscosity of less than about 1000 centistokes at 25° C.

DETAILED DESCRIPTION OF THE PREFERRED EMBODIMENTS

As is understood from the above described summary of the invention, the scope of the invention consists in the use of a specific organosilicon compound, which has never been used hitherto as an insecticide, for the purpose of insecticide against the pests. Namely, the inventors have discovered, as a result of their extensive investigations, that the above specified organosilicon compound can exhibit a very powerful and immediate insecticidal effect against various pests harmful to good sanitation and agriculture and the use of the compound as the insecticide can overcome the problems unavoidable in the prior art insecticide compounds.

The organosilicon compound used as the insecticide in the inventive method essentially has at least one (poly)oxyalkylene group represented by the general formula (I) and denoted by the symbol G in the general formula (II) bonded to the silicon atom in a molecule. The symbol $R^1$ in the formula (I) denotes a hydrogen atom or an organic group which may be a hydrocarbyl or acyl group. The hydrocarbyl group as the group $R^1$ is preferably a lower alkyl group such as methyl, ethyl, propyl, butyl and 2-ethylhexyl groups and the acyl group is exemplified by acetyl and benzoyl groups. The suffixes r, s and t are each zero or a positive integer but s and t cannot be simultaneously equal to zero. When s+t is larger than 1, the group G is a polyoxyalkylene group while the group G better be called an oxyalkylene group when s+t is equal to 1.

The type of the organosilicon compound is not particularly limitative provided that the molecule has at least one (poly)oxyalkylene group of the general formula (I) bonded to the silicon atom. The molecular configuration can be linear chain-like, cyclic, branched or three-dimensionally network forming.

Particularly preferable organosilicon compounds are the organosilane or organopolysiloxane compounds represented by the general formula (II) which represents an organosilane compound when m+n is equal to zero and an organopolysiloxane when m+n is a positive integer. The symbol R denotes a hydrogen atom or a monovalent hydrocarbyl group but the compound should have at least one hydrocarbyl group. Namely, not all of the groups R in a molecule can be hydrogen atoms. Suitable monovalent hydrocarbyl groups include alkyl groups such as methyl, ethyl and propyl groups, cycloalkyl groups such as cyclopentyl and cyclohexyl groups, alkenyl groups such as vinyl and allyl groups, aryl groups such as phenyl and tolyl groups and aralkyl groups such as benzyl and 2-phenylethyl groups. A part or all of the hydrogen atoms in these hydrocarbyl groups may be replaced with substituent atoms or groups such as halogen atoms, cyano groups and the like.

The groups denoted by $G^a$ in the formula (II) are each the same groups as R or the (poly)oxyalkylene group of the general formula (I) denoted by the symbol G in the formula. It is essential, however, that at least one of the two $G^a$ groups in a molecule should be the same as G when the suffix n is equal to zero. In other words, this is an equivalent to the requirement that the organosilicon compound should have at least one (poly)oxyalkylene group of the general formula (I) bonded to the silicon atom in a molecule.

It is preferable that the organosilicon compound should have a viscosity of less than about 1000 centistokes or, more preferably, less than about 100 centistokes at 25° C., especially, when it is an organopolysiloxane compound. When the organosilicon compound is an organosilane compound, the viscosity thereof is usually sufficiently small not to exceed 1000 centistokes at 25° C.

The above defined organosilicon compounds can readily be prepared according to the known procedures described in many patent literatures and textbooks including, for example, Chemistry and Technology of Silicones by Walter Noll, 1968, Academic Press, New York and London.

The method of the present invention is performed by applying the above described organosilicon compound directly to the body of the pest or by distributing the compound over the site or field infested with the pests as a pesticide. It is of course possible that the organosilicon compound is used as such but it is a preferable way that the organosilicon compound as the effective constituent is admixed, according to known procedures and formulations, with various kinds of additives including carriers, extenders, diluents, spreading agents, propellants and the like according to need to form a pesticide composition which may be, for example, in an oily, emulsion-like, powdery, creamy or gel-like form or in the form of an aerosol-type spray suitable for the particular manner of application intended. The method and instrument for applying or distributing the pesticide composition naturally depend on the form of the composition and the species of the pests or the condition of the site or field where the pesticide composition is used.

The organosilicon compounds used as an insecticide in the inventive method are effective to almost all kinds of noxious insects and arachnids including flies, mosquitos, cockroaches, fleas, lice, mites, ticks and the like ectoparasitic and non-ectoparasitic pests harmful to good sanitation and leaf hoppers, cut-worms, diamond-back moths, leaf folders, aphids, rice borers and the like pests in agriculture. Further, the insecticidal effectiveness of the organosilicon compounds is not limited to a specific stage in the whole life cycle of the pests but the compounds are effective throughout the whole stages of the life cycle of the pests including ova or nits, larvae, chrysalises and imagoes.

Following are the examples to illustrate the insecticidal effectiveness of the organosilicon compounds used in the inventive method but not to limit the scope of the invention in any way. In the following Examples, 7 kinds of organosilicon compounds (a) to (g) each expressed by the structural formula

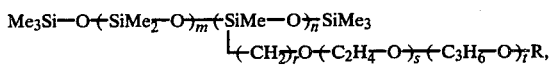

were prepared, in which Me is a methyl group, R is a hydrogen atom, an acetyl group or a n-butyl group as indicated in Table 1 below and each of the suffixes r, s, t, m and n has the value also indicated in Table 1 for each of the compounds. Table 1 also includes the viscosity of each of the compounds in centistokes determined at 25° C.

EXAMPLE 1

15 Individual specimens of final age larvae of housefly and first age larvae of Croton bug were dipped in one of the organosilicon compounds (a) to (g) and immediately taken out thereof followed by removal of the organosilicon compound adhering to the body by wiping with a paper towel. The thus treated larvae were kept at 30° C. and the numbers of the killed individuals were counted after 1 hour to give the results shown in Table 2 below by the percentages of the killed larvae.

TABLE 1

| Compound | r | s | t | m | n | R | Viscosity |
|---|---|---|---|---|---|---|---|
| (a) | 3 | 1 | 0 | 0 | 1 | Hydrogen | 13 |
| (b) | 3 | 4 | 4 | 0 | 1 | Hydrogen | 37 |
| (c) | 3 | 4 | 4 | 10 | 5 | Hydrogen | 98 |
| (d) | 3 | 10 | 0 | 24 | 4 | Hydrogen | 452 |
| (e) | 3 | 18 | 18 | 27 | 3 | Acetyl | 984 |
| (f) | 3 | 26 | 26 | 30 | 3 | n-Butyl | 2017 |
| (g) | 0 | 40 | 10 | 30 | 3 | n-Butyl | 4981 |

The same experimental procedure as above was repeated except that a 50% by weight aqueous solution of each of the organosilicon compounds was used in place of the compound as such. The insecticidal effects were substantially the same as in the use of the undiluted compounds.

TABLE 2

| Organosilicon compound | Housefly larvae killed, % | Croton bug larvae killed, % |
|---|---|---|
| (a) | 100 | 100 |
| (b) | 100 | 100 |
| (c) | 100 | 100 |
| (d) | 95 | 100 |
| (e) | 95 | 95 |
| (f) | 80 | 90 |
| (g) | 80 | 90 |

EXAMPLE 2

15 nits of common gnat and housefly were dipped for 2 minutes in one of the organosilicon compounds (a) to (f) and taken out thereof followed by removal of the organosilicon compound adhering to the nits with a paper towel. The thus treated nits were incubated in a thermostatted room at 30° C. during their respective nit stages and the numbers of the unhatched nits were counted to give the results shown in Table 3 below by the percentages of the unhatched nits.

TABLE 3

| Organosilicon compound | Common gnat nits unhatched, % | Housefly nits unhatched, % |
| --- | --- | --- |
| (a) | 100 | 100 |
| (b) | 100 | 100 |
| (c) | 100 | 95 |
| (d) | 95 | 90 |
| (e) | 95 | 90 |
| (f) | 90 | 85 |

EXAMPLE 3

Each of the organosilicon compounds (a), (b), (c) and (e) was applied to a filter paper in a coating amount of 50 ml/m$^2$ and 10 individual specimens of imagoes of acarid and Croton bug and final age larvae of housefly were released on the filter paper to freely crawl thereon for 1 hour. After 24 hours, the numbers of the surviving individuals were counted to find that all of the individuals which had crawled on filter paper with one of the organosilicon compounds (a), (b) and (c) had been killed, while 90% of the individuals were killed when the filter paper was coated with the organosilicon compound (e).

What is claimed is:

1. A method for controlling insects which comprises applying an insecticidally effective amount of an organosilicon compound of the formula

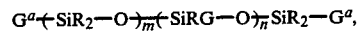

in which m and n are zero or a positive integer,

R may be the same or different and is a hydrogen atom, a hydroxy group or a monovalent hydrocarbyl group, wherein at least one of the groups R is a monovalent hydrocarbyl group selected from the group consisting of alkyl, cycloalkyl, alkenyl, aryl, and aralkyl, G is a (poly)oxyalkylene group having the formula

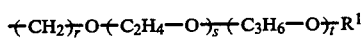

in which R1 is a hydrogen atom, a monovalent hydrocarbyl group selected from the group consisting of alkyl, cycloalkyl, alkenyl, aryl and aralkyl, or an acyl group, and r, s and t are zero or a positive integer, wherein s and t are not simultaneously equal to zero, and $G^a$ is the same group as R or G, and at least one of the groups denoted by $G^a$ is G when n is equal to zero, directly to the insects or a site infested with the insects.

2. The method as claimed in claim 1 wherein the organosilicon compound has a viscosity of less than about 1000 centistokes at 25° C.